United States Patent [19]
Berglund et al.

[11] Patent Number: 6,090,288
[45] Date of Patent: Jul. 18, 2000

[54] PROCESS FOR CHROMATOGRAPHIC SEPARATION OF PEPTIDES AND NUCLEIC ACID, AND NEW HIGH AFFINITY ION EXCHANGE MATRIX

[75] Inventors: Rolf Berglund, Uppsala; Jan Bergström, Bälinge; Makonnen Belew; Lennart Söderberg, both of Uppsala, all of Sweden

[73] Assignee: Amersham Pharmacia Biotech AB, Uppsala, Sweden

[21] Appl. No.: 09/117,678

[22] PCT Filed: Feb. 14, 1997

[86] PCT No.: PCT/SE97/00237
§ 371 Date: Dec. 29, 1998
§ 102(e) Date: Dec. 29, 1998

[87] PCT Pub. No.: WO97/29825
PCT Pub. Date: Aug. 21, 1997

[30] Foreign Application Priority Data

Feb. 19, 1996 [SE] Sweden ................................ 9600590

[51] Int. Cl.[7] .................................................. B01D 15/08
[52] U.S. Cl. ...................... 210/635; 210/656; 210/198.2; 210/502.1; 530/413; 530/416; 521/30; 536/25.4
[58] Field of Search ...................................... 210/635, 638, 210/656, 660, 679, 199.2, 502.1; 521/30; 536/25.4; 530/413, 416, 417

[56] References Cited

U.S. PATENT DOCUMENTS

| | | | |
|---|---|---|---|
| 4,767,670 | 8/1988 | Cox | 210/656 |
| 5,087,359 | 2/1992 | Kakodkar | 210/198.2 |
| 5,147,536 | 9/1992 | Engstrom | 210/198.2 |
| 5,466,368 | 11/1995 | Arvidsson | 210/198.2 |

*Primary Examiner*—Ernest G. Therkorn
*Attorney, Agent, or Firm*—Royal N. Ronning, Jr.

[57] ABSTRACT

Process for separating off a peptide or a nucleic acid by an anion exchanger (I) characterized in that a) the anion exchanger (I) exhibits ligands, which (i) contain a primary, secondary or tertiary amino group and (ii) are covalently bound to an organic polymer (matrix), b) there on a carbon atom at a distance of 2 or 3 atoms away from an amino nitrogen in the ligands is a hydroxyl group or a primary, secondary or tertiary amino group, and c) the maximum elution ionic strength in the pH range 2–14 for at least one of the proteins transferrin, ovalbumin 1, ovalbumin 2, β-lactoglobulin 1 and β-lactoglobulin 2 on the anion exchanger is higher than the elution ionic strength required for a quaternary comparative ion exchanger.

30 Claims, 9 Drawing Sheets

Fig. 1

Fig. 2A Binding strength between TRIS ligand and some proteins at different pH

Fig. 2B Bindning strength between Q-ligand and some proteins at different pH

Fig. 3 Comparison of anion exchanger ligands at pH 6,0

PROCESS FOR CHROMATOGRAPHIC SEPARATION OF PEPTIDES AND NUCLEIC ACID, AND NEW HIGH AFFINITY ION EXCHANGE MATRIX

REFERENCE TO RELATED APPLICATIONS

This application is a 371 of PCT/SE97/00237 filed Feb. 14, 1997.

FIELD OF THE INVENTION AND DEFINITIONS

The present invention relates to weak anion exchangers, i.e. ion exchangers exhibiting protonated forms of primary, secondary or tertiary amino as anion exchanging ligand. The invention is based on our discovery that this type of anion exchangers, when having certain hydrogen binding atoms at a distance of 2 or 3 atoms away from the nitrogen in the weak anion exchanging group of the ligand, can exhibit enhanced binding properties to peptides or nucleic acids. Because the binding is broken by guanidine or urea, this has been construed as a presence of hydrogen bonds between peptide/nucleic acid and anion exchanging ligand.

Our discovery has led to both a new process for separating nucleic acid or peptide, and new ion exchange adsorbents (ion exchanging matrices) which can be used in the method.

By amino group (structures and expression) is meant, if not otherwise stated, a protonated and non-protonated primary, secondary, tertiary amino group as well as a quaternary ammonium group.

By the expression "to separate" is meant removing or separating off one or more nucleic acids/peptides from a more or less complex mixture of substances. Separation can be used in connection with isolation, purification, and analysis of nucleic acid/peptide. Separation is effected by way of substances interacting with the ligands of the anion exchanger. The interaction is different for different substances which leads to separation.

By nucleic acid is meant both RNA and DNA, including single and double stranded or modified forms of these, such as phosphothionate forms which exhibit protecting groups and markers (isotope, biotin, hapten etc.). Nucleic acid can be an oligo- or poly-nucleotide. The number of bases and basepairs, respectively in oligonucleotides is typically $\leq 200$. The invention is preferably applied to isolation and purification of synthetically produced oligonucleotides.

By peptide is meant compounds exhibiting polypeptide structure, i.e. proteins, such as lipoproteins, glycoproteins, proteoglycans etc., and oligopeptides (i.e. peptides having 2–10 amino acids).

PRIOR ART

EP 276,138 and DE 3,935,098 describe anion exchangers exhibiting weak anion exchanging groups having a hydroxyl group at a distance of two carbon atoms away from a nitrogen in the ion exchanging group. The ion exchanging group has been introduced using a bifunctional reagent which, through a silane group couples to a glass matrix and through an epoxide to a primary or secondary amino glass—O—Si—(CH$_2$)$_3$—O—CH$_2$CHOHCH$_2$—NH—(CH$_2$)$_2$—OH Silane structures are relatively unstable and restrict the range of available pH values. EP 276,138 suggests that the matrix also can be an organic polymer. However, concerning organic matrices, it is uncertain if enough stable products can be obtained in the suggested way. Both publications are related to separation of polynucleotides. DE 3,935,098 does also use an eluent which contains the denaturating agent urea. A more detailed explanation is not given.

EP 167,488 also describes ion exchangers exhibiting weak ion exchanging groups having a hydroxyl group at a distance of two carbon atoms away from a nitrogen atom. The ion exchanging group binds through an amide to the matrix. Nothing is mentioned regarding separation of peptides or nucleic acid.

The inventors of EP 276,138 turn down our types of ligands since they find their binding ability too strong. The explanation is wrong which probably also is the reason for them not to understand to utilize the general feature on which the strong binding ability of our novel ligands is based (hydrogen-bonding). Probably, they have not even realized the need for binding at high ionic strength.

There is also a relatively wide range of literature regarding ECTEOLA cellulose for purification of nucleic acid. ECTEOLA cellulose has been produced by coupling triethanolamine, N(CH$_2$CH$_2$OH)$_3$ to cellulose using epoxide. It has been considered that the resulting groups are —CH$_2$CHOHCH$_2$—N$^+$(CH$_2$CH$_2$OH)$_3$, i.e. ECTEOLA cellulose is a strong ion exchanger. However, it has been shown that commercial variants of ECTEOLA cellulose have relatively high buffer capacity at pH 7–10, which indicates presence of weak ion exchanging groups, which in turn means that hydroxyl groups in triethanol amine has been used for binding to cellulose. Ion exchangers based on triethanol amine, which through reaction with epoxide, have been coupled to cellulose are not comprised within the scope of the new matrices of the invention.

Weak ion exchangers with ligands which are polyvalent in relation to an amino group have previously been used for chromatofocusing. By this type of chromatography an internal pH gradient is generated on the column. Adsorption and elution is performed with low ionic strengths, to avoid bound substances to be displaced by salts in the buffer. Presently used ionic strengths for adsorption are <50 mM NaCl, typically <30 mM. For elution the ionic strengths are even lower (5 fold lower). See Sluyterman et al., "Ten years of chromatofocusing: a discussion" (J,. Chromatog. 470(2) (1989) 417–426). According to this definition chromatofocusing is not within the scope of the process of the invention.

SUMMARY OF THE INVENTION

In chromatography there is a general need for obtaining improved methods for separation of peptides and nucleic acid. Especially can be mentioned purification of proteins from supernatants derived from fermentation and other cell culture plants. These media often contain high levels of salt (conductivity $\geq 15$–20 mS/cm) making them difficult to apply directly on conventional ion exchangers. Pretreatment must be done, for example by desalting or dilution, which in turn leads to more expensive process costs. There is also a need for ion exchange adsorbents giving adsorption at high ionic strength, preferably at ionic strengths which correspond to conductivities of $\geq 15$–20 mS/cm, and which can be desorbed at low ionic strengths, for example by a simple adjustment of pH.

Synthetically produced oligonucleotides are often purified on ion exchangers. In addition to the oligonucleotide which is intended to be produced, the synthesis usually also gives shorter variants. Obtained oligonucleotides usually have the terminal protecting group left. This leads to difficulties in purification and processing. It is often desirable to be able to perform chromatography and deprotection in one step.

There is also a desire for improved ion exchange methods, which give improved dynamics, improved capacity and a reduced number of steps for purification and isolation of peptides and nucleic acid.

THE INVENTION

Figure 2A:
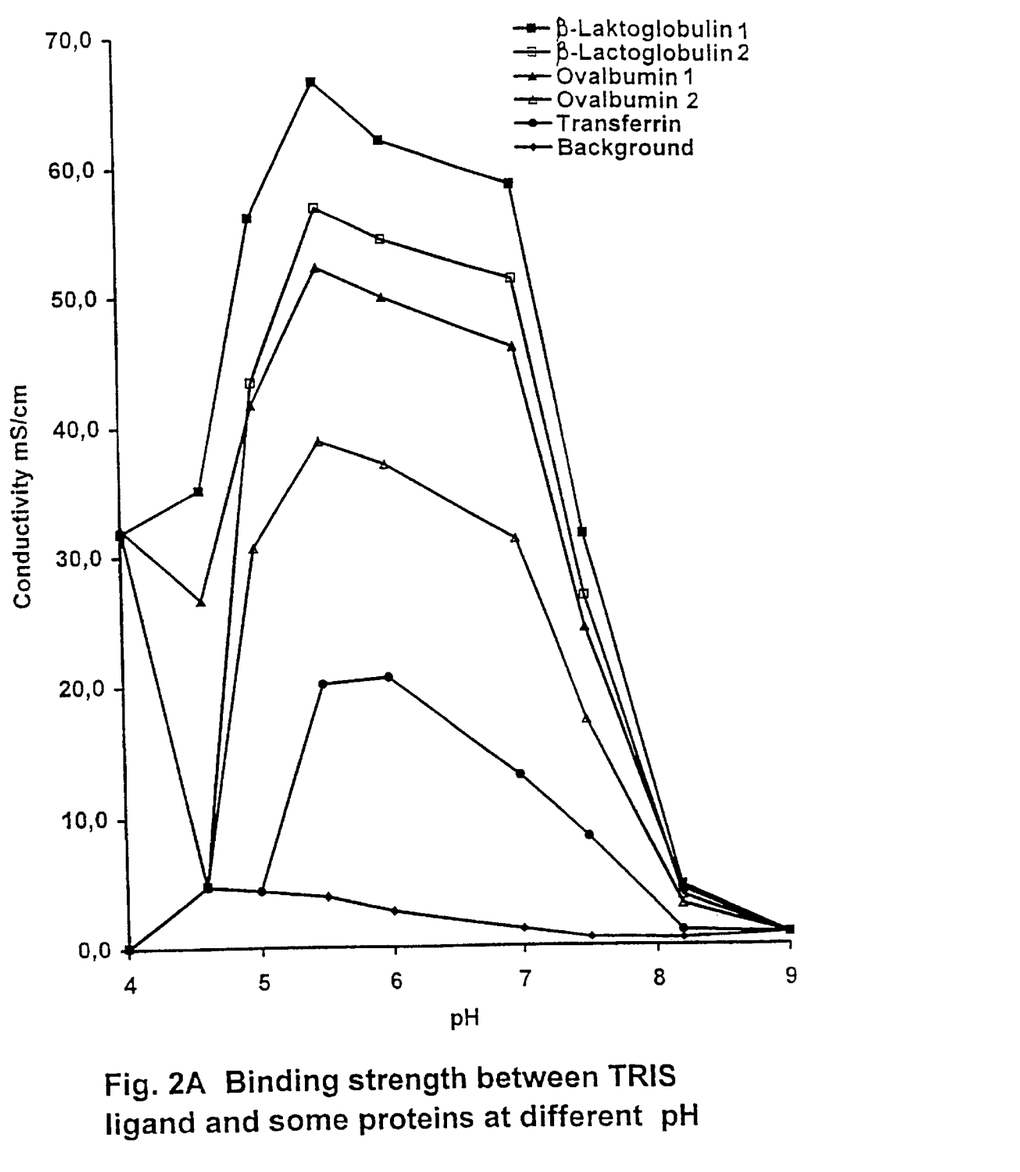
FIGS. 2A and 2B: pH dependence of the elution ionic strength for proteins on above-described agarose gels with tris-ligand (2A) and Q-ligand (2B), respectively.

The discovery of the initially mentioned enhanced binding properties has enabled us to provide anion exchangers (I) showing greater dynamics in the separation of proteins and nucleic acid. This can be expressed in such a way that the maximum elution ionic strength in the pH range 2–14 for the anion exchanger (I) is higher than, in preferred cases >125%, in many cases ≧140%, such as ≧200% of the required elution ionic strength for a quaternary anion exchanger (II) with ion exchanging group $(CH_3)_3N^+$— (=Q-group; the same matrix, same coupling group from the quaternary nitrogen and in towards the matrix, the same level of ligand as for the anion exchanger (I) and measured at the same pH) for desorption of at least one of the proteins given in the experimental part (see FIG. 3), transferrin, ovalbumin 1, ovalbumin 2, β-lactoglobulin 1 and β-lactoglobulin 2). The variation of the elution ionic strength with pH of the anion exchanger that was used according to the invention for certain proteins is illustrated in FIG. 2A.

In the method according to the invention a solution containing the nucleic acid and/or peptide, which is to be separated off, is contacted with an anion exchanger, exhibiting ligands with positively charged amino groups, covalently coupled to a polymer matrix, under such conditions that a desired peptide and/or nucleic acid in the sample separates from at least one further substance in the solution (adsorption step). In case separated peptide/nucleic acid has become adsorbed to the anion exchanger it can, if desired, be desorbed by an eluent. The method is characterized in that the used anion exchanger has amino groups, which are primary, secondary or tertiary, and that on at least one carbon atom, being at a distance of 2 or 3 atoms away from the amino nitrogen in the anion exchanging group, there is a hydroxyl group or a primary, secondary or tertiary amino nitrogen. In the characterized portion of the method is also included that the anion exchanger (I) is selected so that at least one of the proteins given in the experimental part (FIG. 3; transferrin, ovalbumin 1, ovalbumin 2, β-lactoglobulin 1 and β-lactoglobulin 2) requires elution ionic strengths as above.

The solution (including the eluent) applied on the anion exchanger is typically aqueous consisting of water, possibly comprising a liquid miscible with water, for example ethanol, methanol, acetonitrile, mixtures miscible with water etc. The solution may also be any of the above mentioned organic solvents. The solutions, especially eluents, often contain salts, buffer substances, substances which break hydrogen bonds etc.

The solution containing nucleic acid/peptide, can be a supernatant of a cell culture, but can also be a synthesis mixture, possibly partially processed, or an extract. The ionic strength in the solution should be such that it enables the desired binding/adsorption to the ion exchanger. Depending on ion exchanging groups and protein or oligo-/poly-nucleotide, which is to be adsorbed, the ionic strength/conductivity can be higher or lower than 15–20 mS/cm.

Anion Exchangers to be Used According to the Process of the Invention

Preferred anion exchangers are represented by formula I. Several of them are new. The man skilled in the art can by simple experiments in ways that are shown in the experimental part (Experiment 2C) decide whether an ion exchanger meets the above mentioned criteria for elution ionic strength.

FORMULA I ligand      ligand arm (B) plus matrix (M)

— means that the ligand arm replaces a group $R_{1-6}$ or a hydrogen in any of the groups $R_{1-6}$ in the ligand. Preferably the ligand arm is replacing $R_1$ or $R_5$ or $R_6$.

The ligand often has a molecular weight of ≦1000.

M is a matrix and contains additional ion exchanging ligands, typically according to formula I.

n is an integer of 1 or 2, typically 1.

$R_{1-6}$ is selected among hydrogen and linear, branched or cyclic saturated or unsaturated hydrocarbon group, which can be monovalent or divalent. Divalent groups consist of two connected groups $R_{1-6}$, so that a 5 or 6 membered ring is formed together with any of the atoms in formula I marked with bold letters.

Typical examples of pairs of $R_{1-6}$, forming divalent groups, are $R_5$ and $R_6$, $R_1$ and $R_5$ or $R_1$ and $R_6$. In contemplated hydrocarbon groups the carbon chain can be disrupted by one or more amino nitrogen or ether oxygen atoms (—$NR_7$— and —O— respectively) and/or one or more hydrogens can be substituted by an amino group (—$N^+R_8R_9R_{10}$) or by a group —$OR_{11}$. One and the same carbon atom binds, apart from to carbon and hydrogen, typically to maximum one oxygen or nitrogen atom. Contemplated carbon chains, including possible disruptions of oxygen or nitrogen atoms, are generally ≦10 atoms in length, preferably 6 or fewer atoms. $R_{1-6}$ can exhibit one or more ether oxygen atoms, hydroxyl groups or amino nitrogen atoms at a distance of 2 or 3 atoms away from the nitrogen atom, to which $R_5$ and $R_6$ bind (above all in $R_5$ and $R_6$).

$R_1$, $R_3$ and $R_4$ are preferably hydrogen. In the case where n=2, $R_3$ and $R_4$ on one of the carbon atoms can be different from those on the other carbon atom.

Either or both of $R_5$ and $R_6$ can be hydrogen. If either of $R_5$ and $R_6$ is hydrogen it is preferable if the other is unsubstituted alkyl ($C_nH_{2n+1}$— or corresponding cyclic forms $C_nH_{2n}$—; n is an integer, generally 1–10). $R_5$ and $R_6$ can not simultaneously be selected among methyl and ethyl.

Examples of $R_{16}$ are lower alkyl (having 1–6 carbon atoms), such as methyl, ethyl, n-propyl, isopropyl-, n-butyl-, sec-butyl, t-butyl and isobutyl, including corresponding forms substituted by a group —$N^+R_8R_9R_{10}$ or —$OR_{11}$. Exemplary substituted forms are hydroxymethyl; -hydroxyethyl; 2-hydroxypropyl; 2-hydroxy-1-methylethyl; 1-hydroxymethyl-2-hydroxyethyl; 2-hydroxybutyl; 1-(hydroxymethyl)propyl; 1-methyl-2-hydroxypropyl; 2-hydroxy-1,1,-di(hydroxymethyl)ethyl; 1,1-di (hydroxymethyl)ethyl; 1-hydroxymethyl-1-methylethyl; 1,1-di(hydroxymethyl)propyl-; 2,3-dihydroxypropyl; 2,3,4-trihydroxybutyl-; 2,3,4,5-tetrahydroxypentyl and 2,3,4,5,6-pentahydroxyhexyl- and corresponding amino groups where for example —$NH_2$ substitutes one or more —OH.

$R_{7-11}$ are selected among the same groups as $R_{1-6}$, preferably one, two, three or four of $R_{7-11}$ are hydrogen or lower alkyl $C_{1-6}$. In the case where all $R_{8-10}$ are alkyl groups —$N^+R_8R_9R_{10}$ is a quaternary ammonium group.

Divalent hydrocarbon groups which can be formed by pairs of groups $R_{1-6}$ are for example —$CH_2CH_2$— and —$CH_2CH_2CH_2$—; —$CH_2CH_2CH_2CH_2$—; —$CH_2CH_2CH_2CH_2CH_2$—; —$CH_2CH_2OCH_2CH_2$—; —$CH_2CH_2NHCH_2CH_2$—; —$CH_2NHCH_2CH_2$—; —$CH_2OCH_2CH_2$—; —$CH_2CH_2CHOHCH_2CH_2$— and —$CH_2CH_2CH[N^+(CH_3)_3]CH_2CH_2$—.

X is —OH or —$NR_{12}R_{13}$, where $R_{12-13}$ are selected among the same groups as $R_1$, $R_3$, $R_5$, and $R_6$. In the most common case at least one of $R_{12-13}$ is hydrogen, i.e. —$NHR_{12}$ or —$NHR_{13}$.

The ligand arm is an organic structure which is hydrolytically stable under pH conditions normally utilized for anion exchange chromatography, i.e. pH 2–14. The ligand arm lacks typically hydrolytically unstable structures, such as silane, carboxylic acid ester (—COO—) or carboxylic acid amide (—CONH—). The ligand arm is preferably a linear, branched or cyclic saturated or unsaturated hydrocarbon chain, which optionally is broken by one or more ether oxygen- and/or amino nitrogen atoms (—$NR'_7$—) or substituted by one or more groups —$N^+R'_8R'_9R'_{10}$ or —$OR'_{11}$. $R'_{7-11}$ are selected according to the same rules as for $R_{7-11}$. In the most common case $R'_7$, $R'_{11}$ and at least one of $R'_{8-10}$ are hydrogen, preferably two or three. The $R'_{7-11}$, that are not hydrogen, are typically lower alkyl (having 1–6 carbon atoms). One and the same carbon atom in the ligand arm binds, apart from carbon and hydrogen, typically to at the most one oxygen or nitrogen atom.

Preferred ligand arms B often have a length of 0–20 atoms. The ligand arm B often derives from couplings involved in a reactions between epoxide or —$CH_2X'$ (where X'=halogen, which can be replaced by another functionally equivalent group, such as tosylate) and ammonia, primary, secondary amino ($NHR_5R_6$, where $R_5$ and $R_6$ are according to above) or alcoholic hydroxyl. The group —$CH_2X'$ can be included in halohydrin, alkyl halide, vicinal dihalide etc. Preferred couplings is effected via epoxide, halohydrin and vicinal dihalide, as they per se lead to a hydroxyl group that is β (at a distance of 2 carbon atoms away) to an amino group. Coupling via epoxide, halohydrin and vicinal dihalide means that in formula I n=1, X=OH and $R_{3-4}$=H, i.e. the structure nearest to $NR_5R_6$ becomes —$CH_2CHOHCH_2$—. Example of preferred structures —B—$CHXCR_3R_4$— which can be formed as a result of this type of couplings are —$CH_2CHOHCH_2$—O—$CH_2CHOHCH_2$—; —$CH_2CHOHCH_2$—O—$(CH_2)_4$—O—$CH_2CHOHCH_2$—; —$CH_2CHOHCH_2$— etc., i.e. B is —$CH_2CHOHCH_2$—O—$CH_2$—; —$CH_2CHOHCH_2$—O—$(CH_2)_4$—O—$CH_2$—; —$CH_2$—. Epoxide-/vicinal dihalide-/halohydrin groups can be introduced in a known way by allylation of a polymer containing hydroxyl group(s), for example by reaction with allylglycidyl ether, and subsequent halogenation. See e.g. Nochumsson S (EP 87995) and Lindgren G (WO 9404192).

The ligand arm B binds typically to the matrix M through an ether structure where the ether oxygen derives from a hydroxyl in the matrix.

Thioether (—S—) and sulphonamide (—$SO_2NH$—) have comparable hydrolytic stability with ether and can thus equivalently replace ether in the ligand arm or in the groups $R_{1-13}$ or $R'_{7-11}$. Preferred ligands are formed if the following compounds are reacted with matrix bound epoxide/halohalide/vicinal dihalide:

| Compound | Ligand(nonprotonated form) |
|---|---|
| Ammonia | —$CHOHCH_2NH_2$ |
| propylamine | —$CHOHCH_2NHCH_2CH_2CH_3$ |
| triethylenetetraamine | —$CHOHCH_2NHCH_2CH_2NHCH_2CH_2NHCH_2CH_2NH_2$ |
| bisaminopropylamine | —$CHOHCH_2NH(CH_2)_3NH(CH_2)_3NH_2$ or —$CHOHCH_2N[(CH_2)_3NH_2]_2$ |
| t-butylamine | —$CHOHCH_2NH[C(CH_3)_3]$ |
| ethanolamine | —$CHOHCH_2NHCH_2CH_2OH$ |
| diethanolamine | —$CHOHCH_2N(CH_2CH_2OH)_2$ |
| tris(hydroxymethyl)-methylamine | —$CHOHCH_2NHC(CH_2OH)_3$ |
| 2-amino-1,3-propanediol | —$CHOHCH_2NHCH(CH_2OH)_2$ |
| 3-amino-1,2-propanediol | —$CHOHCH_2NHCH_2CHOHCH_2OH$ |
| 2-amino-2-methyl-1,3-propanediol | —$CHOHCH_2NHC(CH_3)(CH_2OH)_2$ |
| 1-amino-deoxysorbitol | —$CHOHCH_2NHCH_2(CHOH)_4CH_2OH$ |
| 2-glucoseamine |  |
| bis-(tris(hydroxy-methylmethyl)amino)propane | —$CHOHCH_2N[C(CH_2OH)_3](CH_2)_3NHC(CH_2OH)_3$ |

The shown ligands have been formed as a result of coupling through the amino nitrogen. Alternatively coupling can be effected at a hydroxyl group, giving other ligands according to formula I. This means that one and the same anion exchanger according to the invention often exhibits one or more ligands according to formula I. The coupling reaction can be directed so that it occurs more or less selective at either the amino nitrogen or the hydroxyl oxygen. It appears that the ligand can contain atoms both from the compound which is coupled to the matrix and from the reactive group utilized for coupling.

At the date of priority, the most preferred ligands for separation of nucleic acid were those which are formed if matrix bound vicinal dihalide, halohydrin or epoxide is reacted with t-butylamine, 2-amino-1,3-dihydroxypropane, tris(hydroxymethyl)methylamine, ethanolamine or n-propylamine.

Figure 3:
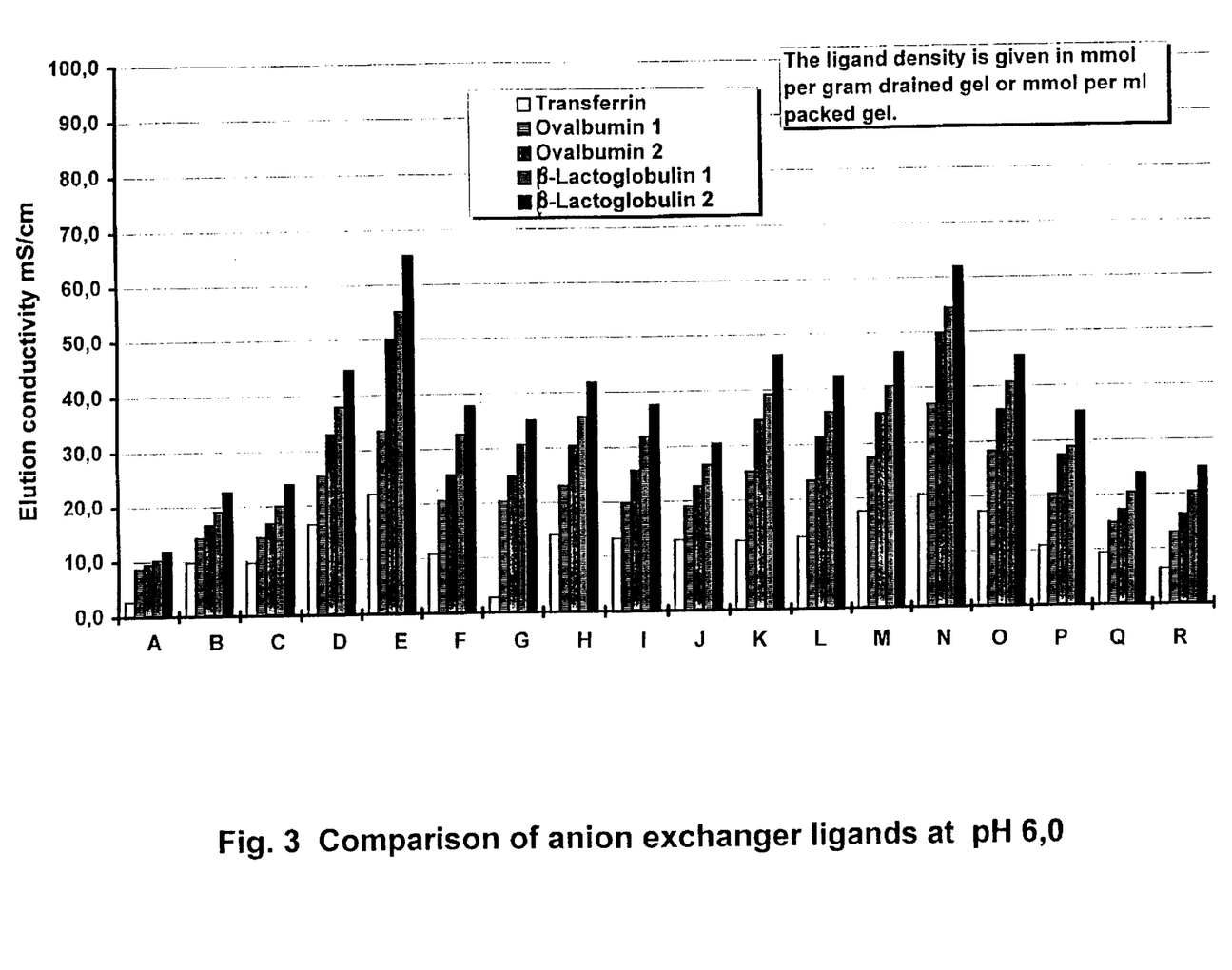
FIG. 3: Elution ionic strengths—comparison between different anion exchange ligands.

The preferred anion exchangers for peptide separation require elution ionic strengths of more than, typically ≧125%, in many cases ≧140%, such as ≧200%, of the elution ionic strength which, according to above, is required for a quaternary ion exchanger with Q-groups for desorption of at least one of the proteins given in the experimental part (FIG. 3).

The matrix M in the invention is generally a hydrophilic polymer insoluble in water, which also includes hydrophobic polymers which have been derivatized so as to be hydrophilic. Examples are polyhydroxy polymers based on polysaccharides, such as agarose, dextran, cellulose, starch, pullulane etc., and purely synthetic polymers, such as polyacrylamide, polymethacrylamide, poly(hydroxyalkyl vinyl ethers), poly(hydroxyalkyl acrylate) and corresponding polymethacrylate, polyvinyl alcohol, and polymers based on styrene and divinylbenzene (DVB), and copolymers where corresponding monomers are included. Polymers soluble in water, can be derivatized to insolubility, e.g. by cross-linking or by attachment via adsorption or covalent binding to an insoluble body. Hydrophilic groups can be introduced on hydrophobic polymers (e.g. styrene-DVB-copolymers) by effecting polymerisation together with monomer, having groups which can be transformed to OH, or by hydrophilization of the final polymer, e.g. by adsorption of suitable compounds, such as hydrophilic polymers. The matrix is often porous to increase the surface, which is contacted with surrounding liquid. Polymer arms (tentacles) can also be included in the matrix, each arm exhibiting one or more ligands bound via the ligand arm B according to formula I.

Preferred matrices lack hydrolytically unstable groups such as silane, ester and amide groups.

The level of ligand according to formula I in the ion exchangers of the invention and in the ion exchangers which can be used in the method of the invention is generally in the range of 0.001–4 mmole, preferably 0.01–1 mmole, per ml matrix saturated with water. Possible and preferred ranges are determined by the structure of the matrix. The level of ligand is thus for agarose-based matrices generally in the range of 0.1–0.3 mmole per ml swelled matrix (gel). For dextran-based matrices the range can be expanded up to 0.5–0.6 mmole per ml swelled matrix (gel). Contemplated levels of ligand are determined in a way that is shown in the experimental part.

The New Anion Exchangers of the Invention

These are according to formula I with the additional conditions that if one or two of the groups $R_5$ and $R_6$ contains one or more nitrogen atoms then at least one of the groups also contains one or more oxygen atoms (—$OR_{11}$, where $R_{11}$ is according to above). Both $R_5$ and $R_6$ and cannot at the same time be selected among methyl and ethyl. Preferred forms of the ion exchangers of the invention exhibit elution ionic strengths according to above. Anion exchangers produced by coupling of triethanolamine via a reaction with epoxide are not a part of this aspect of the invention. The meaning of —, n, B, M, X, $R_{1-4}$, $R_{7-11}$ and $R'_{7-11}$ is the same as for formula I.

Steps of the Method

The adsorption in the process of the invention is performed in a way which has been stated above.

By, after the adsorption step, possibly after intermediate washing, raising the ionic strength in an aqueous eluent and/or adding a denaturating agent and/or by varying pH, it is possible in a known way to selectively desorb substances, which have been adsorbed, for example peptides and nucleic acid, and collect the desired substance in a purified form in the eluate. Changes of ionic strength, presence of denaturating agents and pH can be performed gradually (one or more steps) or in form of a continuous gradient.

Desorption, especially for peptides, can be performed at higher ionic strength than what is required on desorption of the same substance from a quaternary ion exchanger with Q-group according to above.

Typical agents which break hydrogen bonds (denaturating agents) are guanidine and urea. Information regarding agents which break hydrogen bonds see Levine et al., Biochemistry 2 (1963) 168–175. Depending on how tightly the substance to be desorbed binds to the ligand and the choice of agents which break hydrogen bonds, the concentration of agents which break hydrogen bonds may vary from 0 M up to the solubility for respective agent. Typical levels of agents which break hydrogen bonds are in the range of 0.1 M up to 5 M. As an agent which breaks hydrogen bonds on desorption, the ligand of the ion exchanging matrix can also potentially be used in free form or a homologous compound according to the formula

FORMULA II where $R_{1-6}$, n and X have the same meaning as in formula I. Change of pH can per se lead to breaking of hydrogen bonds.

Use of denaturating/hydrogen bond-breaking agents is above all applicable for separation of nucleic acid and can easily be combined with a salt gradient (=conductivity gradient) or changes of pH.

Generally speaking, if the adsorption involves a significant portion of hydrogen bonds, desorption can be performed at relatively low ionic strengths if agents which break hydrogen bonds (e.g. free ligand) are included in the desorption solution or by raising pH so that the ligand is unloaded and the hydrogen bonds are impaired.

Salt desorption (possibly in form of gradient) can be used for both peptides and nucleic acids and means that the concentration of salt (ionic strength) is increased. The increase may vary from 0 M up to the solubility for respective salt. The increase is often in the range of 0.01–4 M.

pH for the initially applied aqueous solution and the eluent may vary. For peptides, which principally are bound to the adsorbent through ionic interaction, the greatest differences in elution ionic strengths for different proteins are obtained at a pH where the weak anion exchanging groups are positively charged and the peptide which is to be separated is negatively charged. This means generally that too high pH values (>10) and too low pH values are to be avoided. The interaction of hydrogen binding character means that the present type of anion exchanger also can bind weakly positively charged proteins (see FIG. 2A).

The pH of the eluent used for desorbing adsorbed nucleic acid/peptide is preferably adjusted so that buffering components not can bind to the ligand of the anion exchanger, i.e. they are positively charged. Suitable buffer components are cationic bases and acids, such as amines, and zwitterions. Buffering components in utilized eluents are typically within the concentration range of 10–50 mM.

The process of the invention according to the above can be seen as using anion exchangers for separation according to the above with the condition that chromatofocusing according to the above and separation on ECTEOLA-cellulose are not included.

The invention can be used for conventional chromatography on a packed and fluidized bed in column, batchwise adsorption procedures etc. The matrices can be in form of particles (beads), monolitic or in form of surfaces (e.g. in sensors).

BRIEF DESCRIPTION OF THE DRAWINGS

I. Results from Chromatography of Proteins

A–C. Q-ligand 0.03, 0.11, 0.17 mmol/ml, respectively

D. ammonia 0.10 mmole/g.

E. bisaminopropylamine 0.31 mmole/g.

F. propylamine 0.13 mmole/g.

G. t-butylamine 0.15 mmole/g.

H. ethanolamine 0.14 mmole/g.

I. diethanolamine 0.15 mmole/g.

J. triethanolamine 0.06 mmole/g.

K. 2-amino-1,3-propanediol 0.14 mmole/g.

L. 3-amino-1,2-propanediol 0.14 mmole/g.

M. 2-amino-2-methyl-1,3-propanediol 0.15 mmole/g.

N. tris(hydroxymethyl)aminomethane 0.12 mmol/g

O. bistrispropane 0.11 mmole/g).

P. aminosorbitol 0.11 mmole/g.

Q. methylmorpholine 0.12 mmole/g.

R. morpholine 0.28 mmole/g

II. Results from Chromatography of Nucleic Acid

DESCRIPTION OF THE PREFERRED EMBODIMENTS

EXPERIMENTAL PART

1. Synthesis of Ion Exchanger

A. Standard Method (Ion Exchanger of the Invention)

Cross-linked agarose (30 μ particles) prepared by reaction between epichlorohydrin and agarose in the presence of NaOH according to Porath et al (J. Chromatog. 60 (1971) 167–77 and U.S. Pat. No. 3,959,251) was reacted with allylglycidyl ether with NaOH as a base to a allyl level (CH$_2$=CHCH$_2$OCH$_2$CHOHCH$_2$—) of 0.18–0.22 mmole/ml). 40 g of the cross-linked allylated agarose washed with water was added together with 160 ml distilled water and 9.2 g sodium sulphate in a 400 ml beaker equipped with a suspended magnetic stirrer, after which bromine water was added to remaining yellow dyeing. Reduction of excess of bromine was effected with sodium formate, after which the gel was washed with distilled water (>5 bed volumes), dry suctioned for 15–30 seconds. Subsequently the brominated gel was added together with 60 ml distilled water and 60 g tris(hydroxymethyl)aminomethane (=tris, gives the ligand (HOCH$_2$)$_3$CH$_2$NCH$_2$CHOH— (according to formula I, herein below this ligand is called tris-ligand and the ion exchanger is called tris-ion exchanger) in a 3-necked 100 ml Bellco-flask with suspended magnetic bar. Initially the pH was 10.9. The reaction was continued over night (23 hours) at 40° C. pH after completion of reaction time was 10.0. Subsequently, the gel was washed thoroughly with distilled water (>10 bed volumes) and possible storage was conducted in distilled water containing 23% (w/w) ethanol.

Inflection point titration directly on the substituted matrix with NaOH-solution gave a level of ligand of 0.13 mmole/g dry suctioned gel.

Starting from cross-linked allylhydroxypropyl agarose, according to above, ammonia (0.10 mmole/ml), bisaminopropylamine (0.31 mmole/ml), propylamine (0.13 mmole/ml), t-butylamine (0.15 mmole/ml), ethanolamine (0.14 mmole/ml), diethanolamine (0.15 mmole/ml), triethanolamine (0.06 mmole/ml), 2-amino-1,3-propanediol (0.14 mmole/ml), 3-amino-1,2-propanediol (0.14 mmole/ml), 2-amino-2-methyl-1,3-propanediol (0.15 mmole/ml), bistrispropane (0.11 mmole/ml), aminosorbitol (0.11 mmole/ml) and methylmorpholine (0.12 mmole/ml) were coupled in an analogous way. The ion exchange capacity is put within brackets for each complete ion exchanger.

B. Quaternary Ion Exchanger (Q-ion Exchanger; Comparative Ion Exchanger)

These were prepared from cross-linked agarose produced according to the above, substituted with allyl-groups in an amount that matched predetermined ion exchange capacity. The allylated agarose was treated with bromine and reacted with trimethylamine. Ion exchangers having three capacities were prepared (0.03 mmole/l, 0.11 mmole/l and 0.17 mmole/l).

C. Determination of Level of Ligand

Inflection point titration under conditions of equilibrium directly on the ion exchanger in the pH range of 2–11 for weak ion exchangers. Strong ion exchangers were saturated with Cl$^-$ and the excess was washed off with distilled water, after which adsorbed chloride ion was eluated with a solution of AcO$^-$ and was determined by AgNO$_3$ titration of the eluate.

2. Chromatography (Proteins)

A. Chromatography for Comparison of Above-Described Agarose Gel with Tris Ligand and with Q-Ligand Q-Sepharose® HP (Pharmacia Biotech, Uppsala, Sweden) with a capacity of 0.17±0.3 mmole/ml, and the same coupling chemistry and matrix as in experiment 1 B.

Gel according to above was packed in a HR 5/5 column (Pharmacia Biotech AB) to a gel height of 5–6 cm with a back pressure of about 5 bar.

Sample: transferrin 1 mg/ml, ovalbumin 2 mg/ml, lactoglobulin 2 mg/ml, loop volume 50 μl Buffer A: piperazine 20 mM, pH 6.0

Buffer B: piperazine 20 mM, NaCl 1.0 M, pH 6.0

Figure 1:
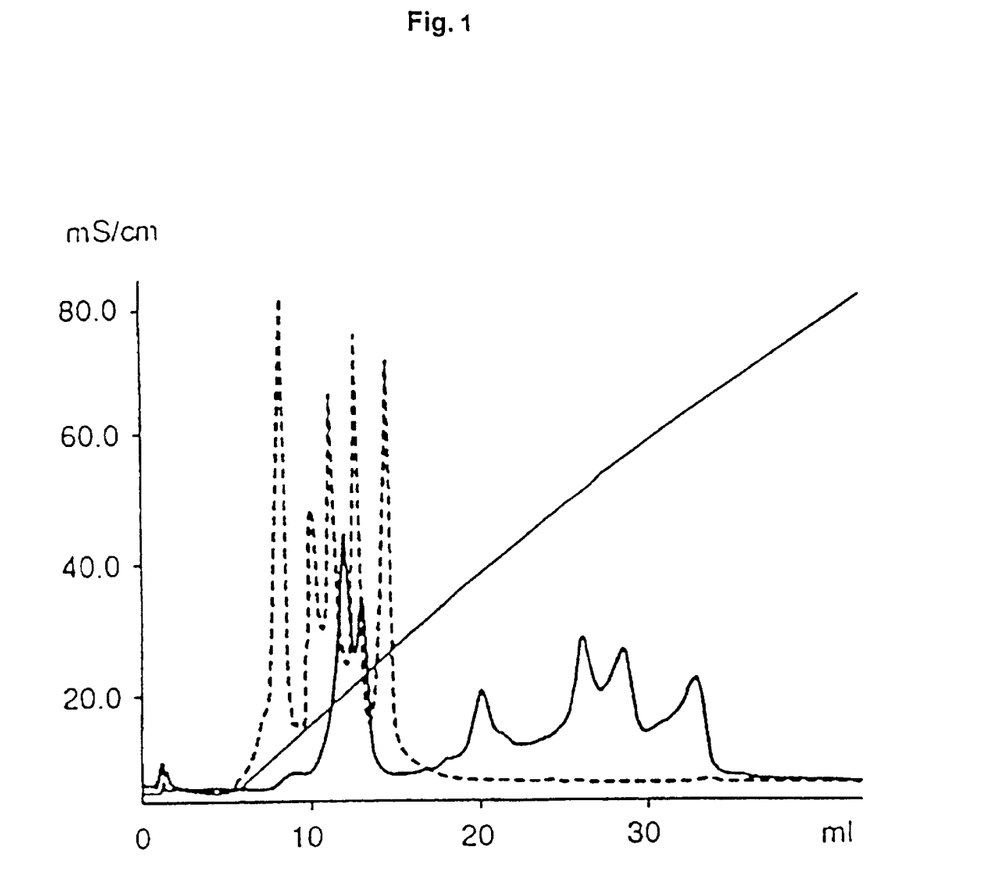
FIG. 1: Chromatography for comparison of agarose gel with tris-ligand described above (ligand according to formula I=(HOCH$_2$)$_3$CH$_2$NCH$_2$CHOH—, ligand arm —CH$_2$OCH$_2$CHOHCH$_2$—) and with Q-ligand (ligand= (CH$_3$)$_3$N$^+$CH$_2$CHOH—, ligand arm —CH$_2$OCH$_2$CHOHCH$_2$—). Broken line chromatogram refers to Q-ligand (Q-Sepharose® HP, Pharmacia Biotech AB, Uppsala, Sweden). Solid line chromatogram refers to tris-ligand.

Flow: 0.2 ml/min
Gradient volume: 40 ml
UV-detector: 280 nm 0.05 AU
Conductometer Maximum=100 mS/cm
Result: The tris-ion exchanger gave considerably higher dynamics as compared to the quaternary ion exchanger. See FIG. 1

Figure 2B:
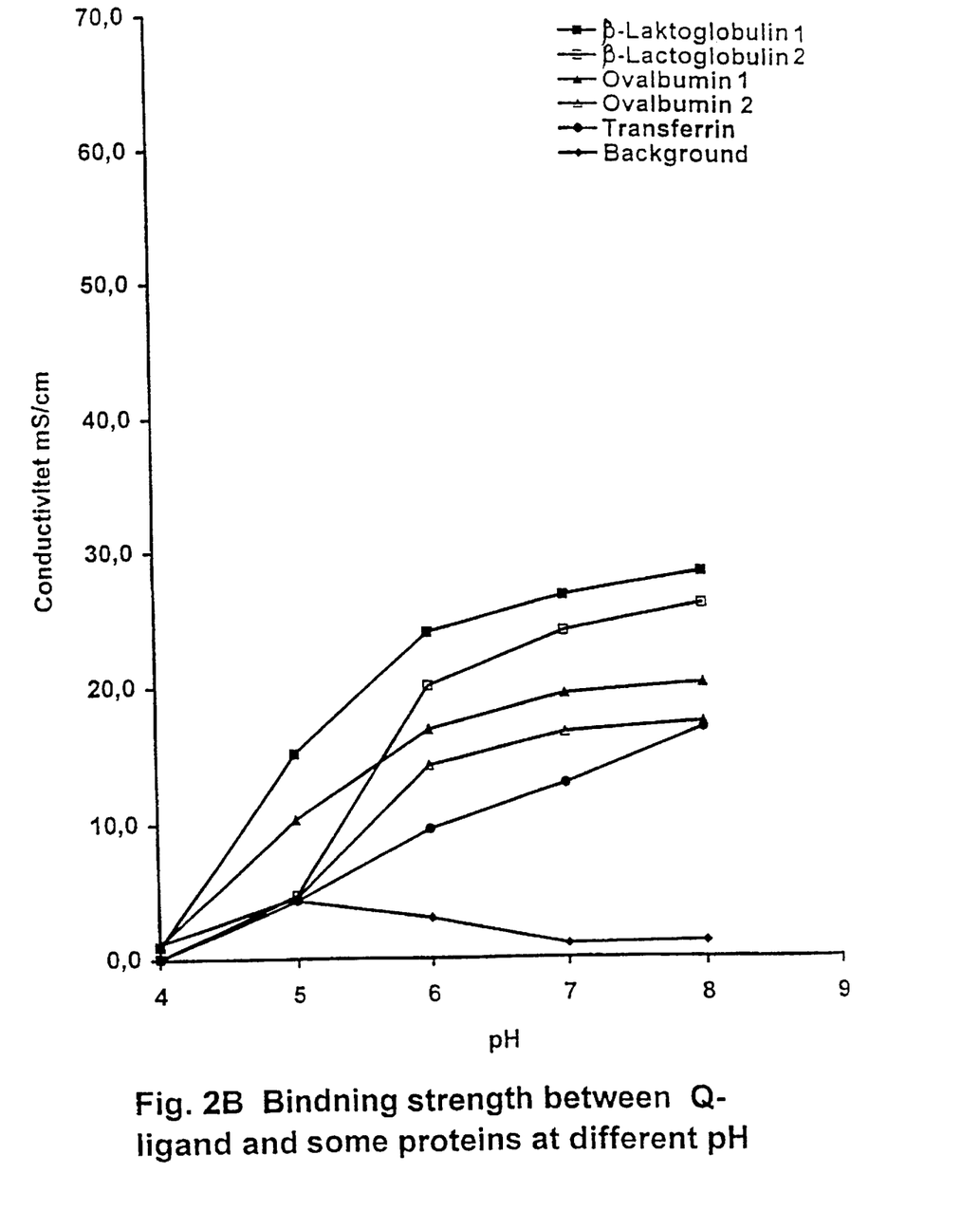

B. pH Dependence of the Elution Ionic Strength for Proteins on Above-Described Agarose Gels with Tris-Ligand and Q-Ligand respectively Column and gel according to 2 A. Flow 1 ml/min. Gradient: 20 ml to 0.5 M NaCl (40 ml to 1.0 M NaCl where appropriate). Samples are evident from FIGS. 2A and 2B.

Buffer by respective pH.
pH 4 Hepes 20 mM-HCl
pH 4.6 piperazine 20 mM-HCl
pH 5 piperazine 20 mM-HCl
pH 5.5 piperazine 20 mM-HCl
pH 6 piperazine 20 mM-HCl
pH 7 Bes 20 mM
pH 7.5 Hepes 20 mM-NaOH
pH 8.0 Hepes 20 mM-NaOH
pH 8.2 tris 20 mM-HCl
pH 9 taurine 20 mM-NaOH Result: See FIGS. 2A and 2B in which conductivity at top maximum is plotted versus pH. FIG. 2A shows the elution ionic strength for the different proteins on the quaternary ion exchanger and FIG. 2B on the tris-ion exchanger. It is apparent that the elution ionic strength for the tris-ion exchanger in the pH range of 6±1 is considerably higher than for the quaternary ion exchanger. Moreover, the difference between elution ionic strength for the protein binding most tightly to the gel and the one binding most weakly is considerably higher on the tris-ion exchanger than on the quaternary ion exchanger (up to pH about 7.5). This shows that it is possible to increase the dynamics in the separation (greater range of ionic strength) by utilizing weak ion exchangers according to the invention.

C. Comparison Between Different Anion Exchanging Ligands Coupled to Cross-Linked Agarose Gel According to Above Column according to 2 A. Gel according to 1 A.
Samples: Transferrin (1 mg/ml), ovalbumin (1 mg/ml), β-lactoglobulin (1 mg/ml).
Buffer A: Piperazine 20 mM pH 6.0
Buffer B: Piperazine 20 mM, NaCl 1.0 M or 0.5 M, pH 6.0
Gradient volume: 40 ml (to 1 M) and 20 ml (to 0.5 M) respectively
Other parameters as above.

Result: FIG. 3 shows the elution ionic strength in mS/cm at pH 6.0 for prepared ion exchangers for the studied model proteins. It is apparent that ion exchangers exhibiting a primary or secondary amino group at a distance of two carbon atoms away from a hydrogen binding group is distinguished from quaternary ligand for ability to separate the studied model proteins from each other by means of anion exchange chromatography.

3. Chromatography (Nucleic Acid)

Material
Ligands: Experiments have been conducted with the same ligands as for proteins. Only results for tris-ion exchangers are presented.
Columns: HR 5/5 column packed to a bed volume of about 1 ml.

Buffers:
A. 20 mM sodium phosphate, pH 7.0.
B. 2 M NaCl in buffer A, pH 7.0.
C. 2 M NaCl & 4 M urea in buffer A, pH 7.0.
D. 4 M urea in buffer A, pH 7.0
E. 20 mM Gly/NaOH, pH 9.0.
F. 2 M NaCl in buffer E, pH 9.0.

Sample: Synthetic phosphorothioate 25-mer oligonucleotide (mol weight 7 500 dalton) with a removed protecting group (trityl). Concentration was 1.08 mmole/ml (8.1 mg/ml) and conductivity about 2 mS/cm. After synthesis and deprotection of trityl group the sample was rotation evaporated (to remove ammonia) and redissolved in deionized water. pH in the solution was typically adjusted to 8.2 before the sample was applied on the packed column (HR 5/5, bed volume 1 ml).

Test Protocol with Results

The sample (2 ml containing 16 mg synthetic oligonucleotide, total $A_{260}$=440) was applied to the column (HR 5/5, $V_t$=1 ml), which was pre-equilibrated with buffer A or buffer E, which was followed by washing of unbound components with buffer A or E. Elution was conducted with buffer B and buffer C (for runs at pH 7.0) or with buffer F (for runs at pH 9.0) (elution rate 153 cm/h, temperature 21° C). The eluate was collected as fractions A, B, C etc. Absorbance at 260 nm was measured for each fraction. The percentage distribution in relation to the total absorbance applied to the column was calculated for each fraction. Collected fractions were desalted on Sephadex® G-25 equilibrated with deionized water. A suitable volume of each fraction was then analysed by capillary electrophoresis to determine purity.

Experiment 1. Elution pH 7

Figure 4:
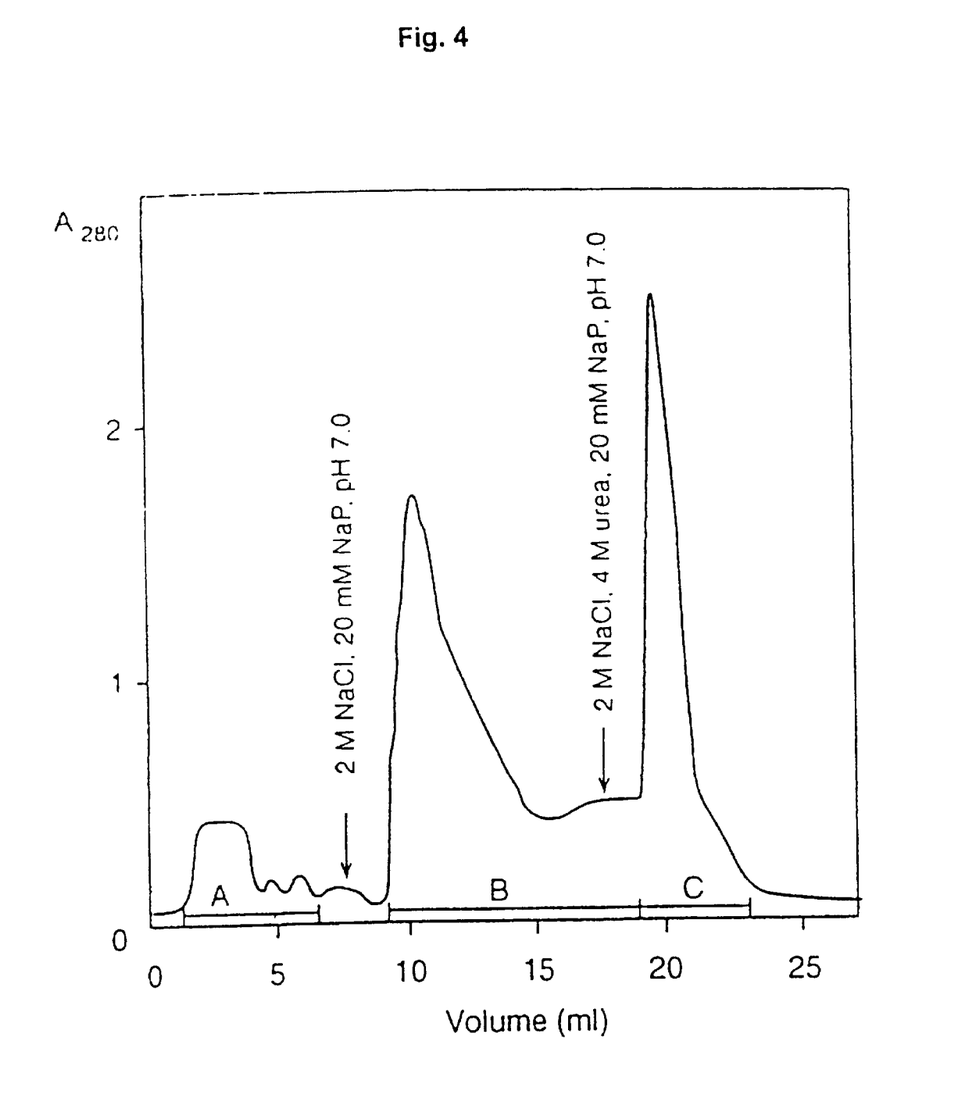
FIG. 4: Experiment 1. Elution at pH 7 with salt followed by urea.

Elution course see FIG. 4. The sample was applied on a column equilibrated with buffer A. After elution of unbound material (fraction A,) with equilibration buffer, bound material was eluted with buffer B (fraction B) followed by buffer C (fraction C). Based on absorbance measurements at $A_{260}$ the distribution of oligonucleotide was: fraction A 6%, fraction B 32% and fraction C 62%. Analysis by capillary zone electrophoresis of fractions B and C showed that fraction B almost exclusively contained low molecular contaminants while fraction C contained 25-mer with a purity of at least 90%. The fact that this fraction was eluted with buffer containing 2 M NaCl and 4 M urea indicates that ionic and hydrogen bonds are involved in binding of oligonucleotide to the weak anion exchanger at pH 7.

The experiment was repeated with the double amount of sample (32 mg 25-mer). The results were generally the same as previously and show that the anion exchanger has high adsorption capacity for this type of oligonucleotides. The counterpart to fraction C showed even higher purity, which can indicate sample-sample displacement with improved purity for the most tightly bound component (in this case 25-mer).

Experiment 2. Effect of Urea, Elution pH 7

Figure 5:
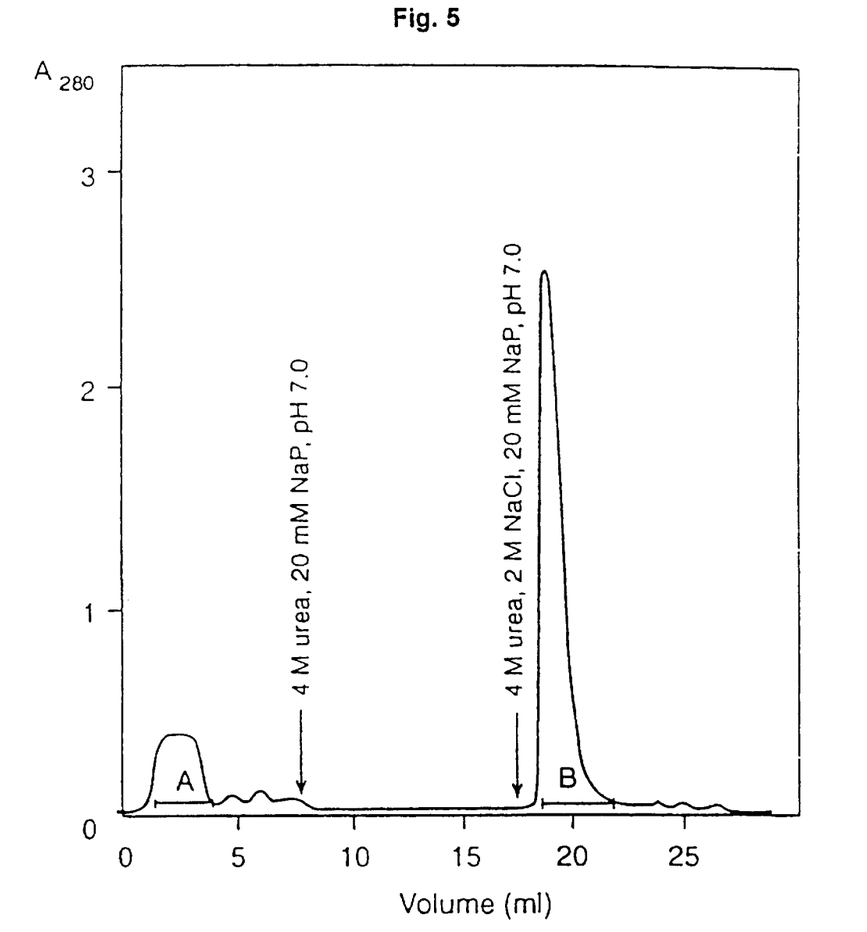
FIG. 5: Experiment 2. Elution at pH 7 with urea followed by salt.

The elution pattern is apparent from FIG. 5. In this experiment, experiment 1 was repeated except that, after washing with equilibrium buffer, the column was first eluted with buffer D (4 M urea) and then with buffer C. FIG. 4 shows that small amounts of unbound material was washed with equilibrium buffer (fraction A), that no bound components were eluted only with buffer D but that quantitative elution was obtained with buffer C (fraction B). The results support that the binding to a the weak anion exchanger is effected via interaction of ionic and hydrogen binding.

Percentage distribution between the fractions was—fraction A 6% and fraction B 93%. Analysis by capillary electrophoresis showed that fraction B was 78% pure 25-mer with several small low molecular peaks. It is evident that an intermediate washing of the column with 2 M NaCl (buffer B, see experiment 1) results in elution of the majority of low molecular compounds and a high purity of 25-mer in fraction C.

Experiment 3. Gradient Elution at pH 7

Figure 6:
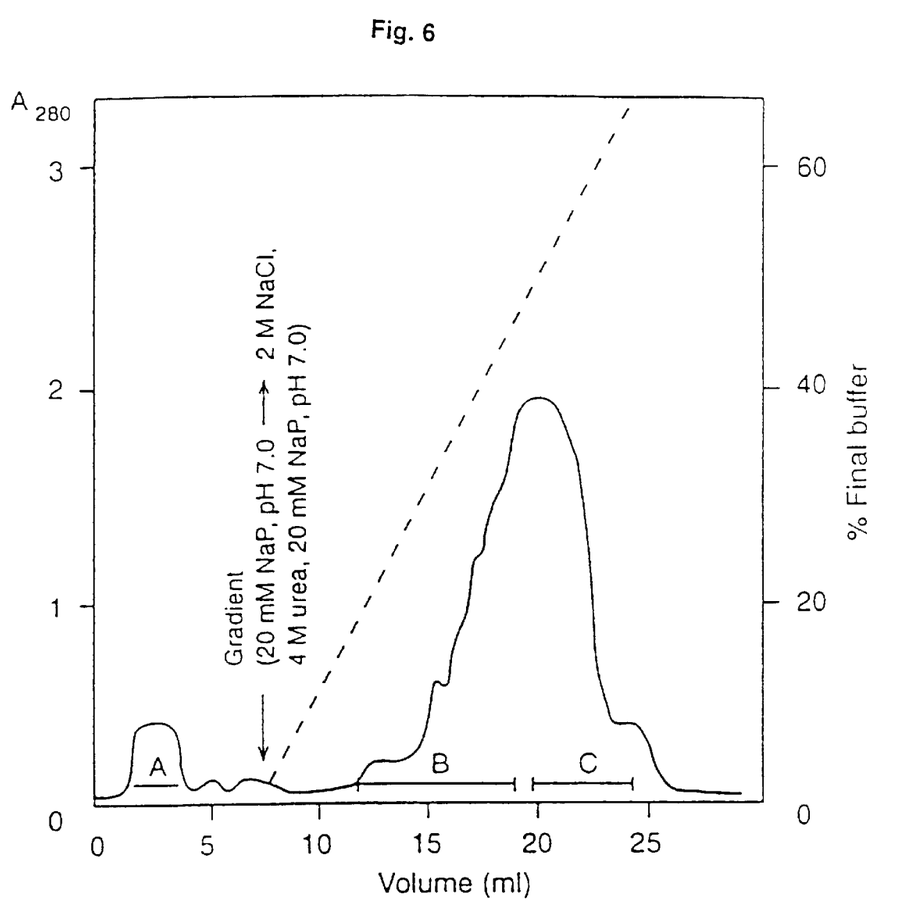
FIG. 6: Experiment 3. Elution at pH 7 with salt gradient

The elution pattern is apparent from FIG. 6. In this experiment, experiment 1 was repeated except that, after washing with equilibrium buffer, the column was eluted with a linear gradient from buffer A to buffer C (where in the concentration of NaCl & urea was increased simultaneously and linearly) or from buffer D to buffer C. In the latter case the column was first washed with buffer D to equilibrate it with the buffer containing 4 M urea. In both experiments elution of bound material occurred as a broad peak with several shoulders, especially in the front-part. This peak was collected as two fractions (fraction B and fraction C, fraction A was material following after washing with equilibrium buffer). Analysis by capillary zone electrophoresis showed that the front-part (fraction B) contained the majority of the low molecular contaminants with a purity for 25-mer of about 40%. The later part of the elution curve (fraction C) contained almost exclusively 25-mer oligonucleotide with a purity of approximately 94%.

Experiment 4. Elution at pH 9

Figure 7:
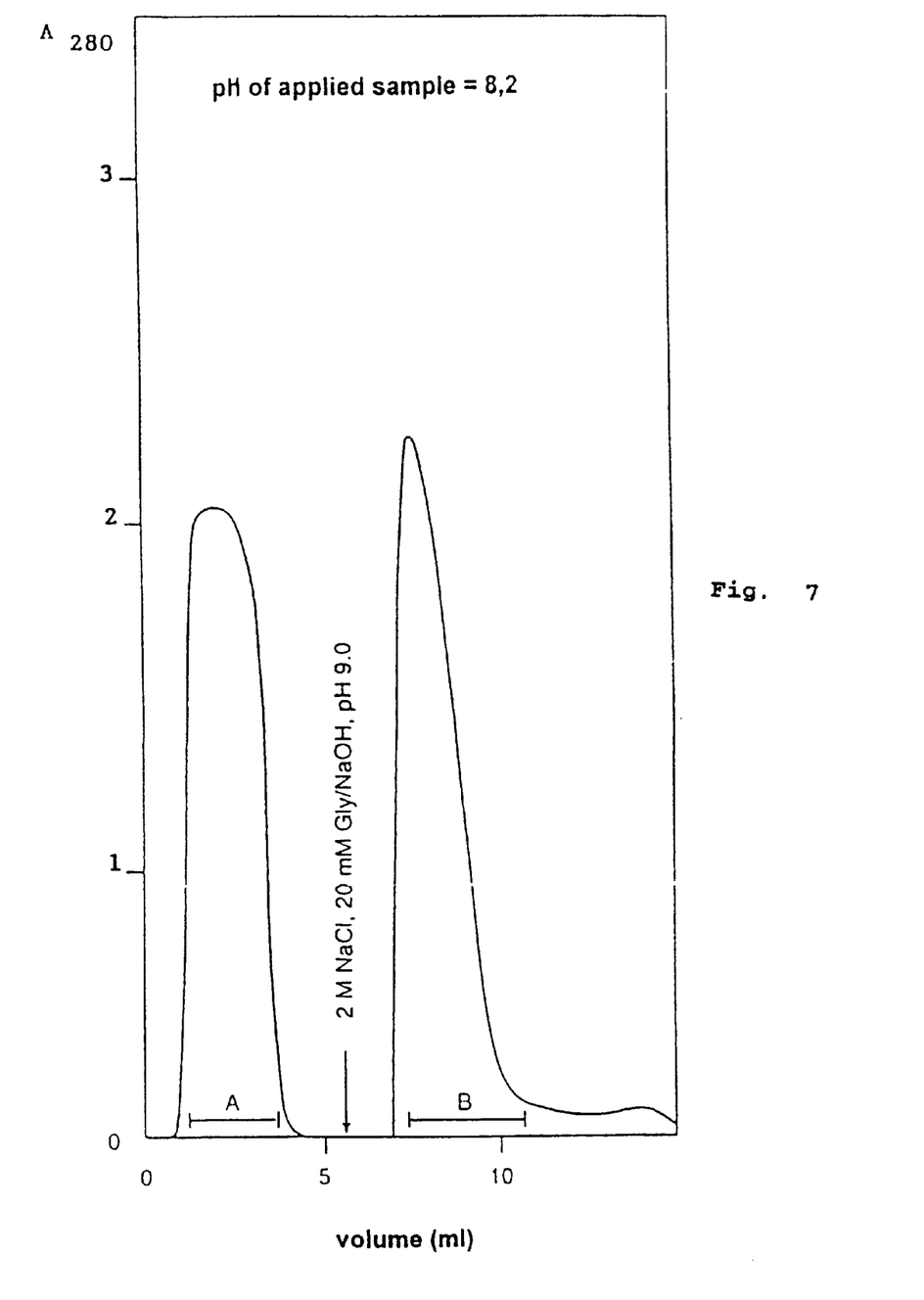
FIG. 7: Experiment 4. Elution at pH 9 with salt. pH for loaded sample 8.2.

Experiment 1 was repeated, with the exception that adsorption and elution of the mixture of oligonucleotides was performed at pH 9 using buffer E and F. pH of the sample was adjusted to pH 8.2 and 2 ml (16.2 mg oligonucleotide) was applied to the column, which had been equilibrated with buffer E. After elution of the unbound fraction (A) with buffer E, bound components (fraction B) were eluted with buffer F. Based on $A_{260}$ for fractions A and B percent distribution was calculated to 47% in fraction A and to 49% in fraction B. The elution pattern is shown in FIG. 7. The obtained result shows:

1. Opposed to the results for elution at pH 7, the bound components were eluted completely with 2 M NaCl (buffer F). At this pH the oligonucleotides seemed to be bound exclusively by ionic interaction without any hydrogen bonds.
2. Analysis by capillary electrophoresis showed that the unbound components (fraction A) contained contaminants and that fraction B had a purity of at least 60%. The purity of fraction B was increased to about 90% if it was eluted with a linear gradient from buffer E to buffer F.

Experiments 5 and 6. (Significance of the pH of the Sample)

It was noted that separation of oligonucleotides at pH 9 was not reproducible. This was principally due to pH differences in the sample applied to the column, which can be seen from the elution pattern in FIGS. 8A and 8B. The experiments are identical with experiment 4 above.

Figure 8A:
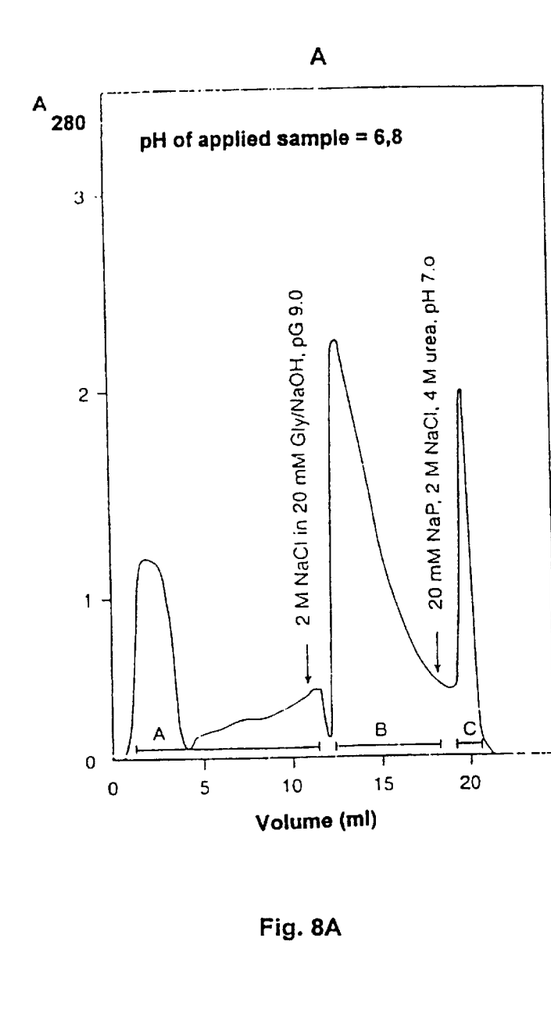
FIG. 8A: Experiment 5. pH for loaded sample 6.8. Elution with salt followed by salt plus urea.

FIG. 8A shows the elution pattern obtained when pH of the applied sample was 6.8. Approximately 75% of the bound components were eluted by buffer F but a lesser part (fraction C, 10% of applied $A_{260}$) is apparently so tightly bound that it requires buffer F for elution. The result is similar to the one obtained in experiment 1 and indicates that applied oligonucleotides are bound to the anion exchanger by ionic and hydrogen bond forces. This can be due to the high density of charged groups on the oligonucleotides, which in turn gives them a high buffer capacity. The result could be that the pH of the anion exchanger actually is lower than equilibrium-pH, when the solution of nucleotides (adjusted to pH 6.8) passes through the same. This hypothesis is probable since tris(hydroxymethyl)aminomethane is weakly dissociated at pH 9. Our results support this hypothesis, since pH in the unbound fraction (fraction A) was 8.9 while pH for the bound fraction (B) was 8.2, though pH in the elution buffer was 9.0 throughout the experiment.

Figure 8B:
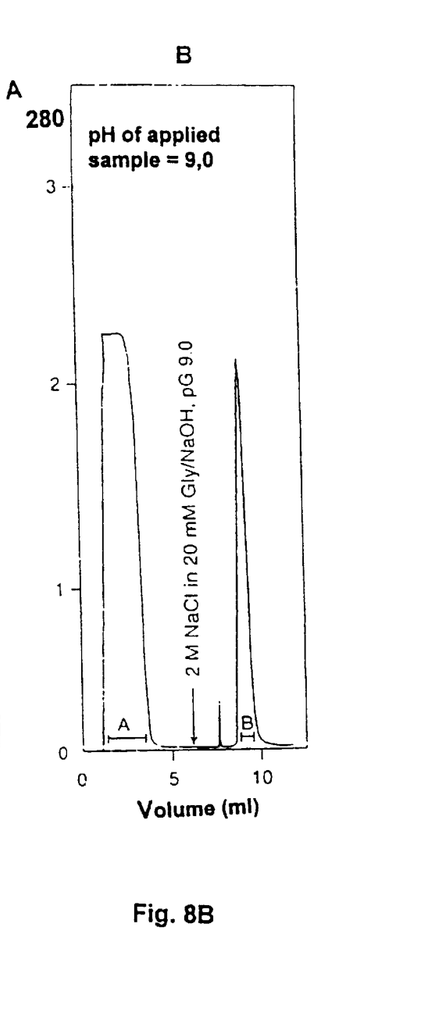
FIG. 8B: Experiment 6. pH for loaded sample 9.0. Elution with salt.

FIG. 8B shows the elution pattern obtained when pH of the loaded sample was 9.0. In this case most of the loaded sample was unbound (88%) and about 10% was eluted with buffer F. This is clearly opposed to the results in FIG. 8A and shows that the oligonucleotides only are bound to the anion exchanger via ionic forces. The binding capacity of the anion exchanger is significantly lowered since tris(hydroxymethyl)aminomethane is only weakly ionized at this pH.

The results obtained in experiment 5 show that separation of oligonucleotides on the tris-ion exchanger used is influenced by the pH of the sample as well as pH of the anion exchanger. The pH value can be varied between 7 and 9 for optimizing purification of a crude product containing a mixture of synthetically produced oligonucleotides.

Experiment 7. Elution with a Linear pH Gradient

Experiment 1 was repeated, with the exception that, after elution of the unbound fraction A, oligonucleotides which bound to the matrix were eluted by a linear gradient (10 bed volumes) of buffer A (pH 7.0) to buffer F (pH 9.0). The result showed that bound oligonucleotides started eluting from the matrix when pH of the effluent was about 8.5. The eluted peak was broad and the purity of the strongly bound component was comparable to the one obtained in experiment 3 above. The result shows that the synthetic oligonucleotide (25-mer) is bound to the matrix by a combination of ionic and hydrogen bonds up to pH 8.5 and by ionic interactions only at higher pH values.

Experiment 8. Competing Elution with Tris-HCl Buffer

The object of this experiment was to investigate if a high concentration of Tris-HCl buffer (1 M, pH 7.0) could displace oligonucleotides bound to the matrix. The column was equilibrated by 50 mM Tris-HCl buffer (pH 7.0 (buffer I), and 2 ml of the sample was applied to the equilibrated column (compare experiment 1 above). After elution of the unbound fraction (A) by equilibration buffer, the column was washed with the following buffers in the following order:

Buffer II: 3 M NaCl in equilibration buffer (buffer I)
Buffer III: 1 M Tris-HCl buffer, pH 7.0, and
Buffer IV: 2 M NaCl, 1 M Tris-HCl, pH 7.0.

The result showed that, of the loaded material:
1. 12.5% did not bind to the column
2. 43% was eluted by buffer II
3. 34% was eluted by buffer III
4. 11% was eluted by buffer IV.

Thus it is clear that the majority of the tightly bound oligonucleotides (about 34%) is eluted with 1 M Tris-HCl buffer, pH 7.0. The most likely explanation for this is that the combination of tris(hydroxymethyl)methylamine and the counter ion Cl⁻ does weaken hydrogen bonds and ionic bonds, respectively, between the ligand and bound oligonucleotides. This explanation is in line with the proposed mechanism for adsorption of oligonucleotides to tris-ligand and its analogs. The result also shows that higher ionic strength (see buffer IV) is required for eluting the most tightly bound fraction. This gives further support to our hypothesis, that binding at pH 7.0 of synthetic oligonucleotides to matrix, exhibiting tris-ligand, is due to ionic interaction with considerable enhancement through hydrogen binding.

Experiment 9. Separation of "trityl-on" from "trityl-off" Synthetic Oligonucleotides This experiment was performed at pH 9.0 and followed the procedure given in experiment 4 above. The crude sample contained a mixture of "trityl-on" and "trityl-off" synthetic oligonucleotides. Approximately 16 mg of the sample in 1 ml deionized water was applied to the column and the experiment was run according to experiment 4. Elution with buffer E (2 M NaCl in 20 mM Gly/NaOH buffer, pH 9.0) gave two well separated fractions (designated B and C). Percentage distribution of material absorbing at 260 nm ($A_{260}$) in the pooled fractions was: fraction A=14%, fraction B=45%, and fraction C=44%. Analysis by capillary zone electrophoresis showed that fraction A exclusively contained low molecular contaminants, fraction B contained mainly the "trityl-off" variant of the synthetic oligonucleotide with a purity of 80%, and the most retarded fraction C had a purity of at least 80% and contained the "trityl-on" variant of the 25-mer oligonucleotide.

This result, together with the earlier described, illustrate the great potential of the invention as a chromatography method for readily purification of synthetic oligonucleotides in high yield and with high purity. By choosing optimal pH condition during the adsorption process the capacity for oligonucleotide of the matrix used can be higher than 20 mg/ml adsorbent.

What is claimed is:

1. Process for separating off a peptide or a nucleic acid, comprising contacting an aqueous solution containing the peptide or the nucleic acid with an anion exchanger (I) under such conditions that the anion exchanger (I) binds substances in the solution so that the desired peptide or nucleic acid is detached from at least one substance in the solution, characterized in that a. the anion exchanger (I) exhibits ligands, which
      i. contain a primary, secondary or tertiary amino group and
      ii. are covalently bound, through an organic bridge, to an organic polymer (matrix),
   b. on a carbon atom at a distance of 2 or 3 atoms away from an amino nitrogen there is a hydroxyl group or a primary, secondary or tertiary amino group, and
   c. the maximum elution ionic strength in the pH range 2–14 for at least one of the proteins transferrin, ovalbumin 1, ovalbumin 2, β-lactoglobulin 1 and β-lactoglobulin 2 on the anion exchanger (I) is at least 125% of the required elution ionic strength required for a quaternary anion exchanger (II) with Q-group (($CH_3$)$_3N^+$—; the same matrix, the same coupling group from the quaternary nitrogen and in towards the matrix, the same level of ligand as for the anion exchanger (I) and the elution ionic strength measured at the same pH for anion exchangers I and II, with the provisos that chromatofocusing and separation on anion exchangers prepared by coupling of triethanol amine to cellulose via reaction with epoxide are not included.

2. Process according to claim 1, characterized in that the anion exchanger has the structure

FORMULA I ligand      ligand arm (B) plus matrix (M)

wherein
   a. — means that the ligand arm B is replacing a group $R_{1-6}$ or a hydrogen in any of the groups $R_{1-6}$ in the ligand,
   b. M is a polymer matrix containing further anion exchanging ligands,
   c. B is an organic structure which lacks hydrolytically unstable structures, and which contains hydrocarbon chains selected among the same carbon chains as $R_{1-6}$,
   d. n is an integer of 1 or 2, typically 1,
   e. $R_{1-6}$ are selected among hydrogen or linear, branched or cyclic saturated or unsaturated hydrocarbon group, which can be monovalent or bivalent, with a carbon chain which optionally is disrupted by one or more amino nitrogen- or ether oxygen atoms (—$NR_7$— and —O— respectively) and/or has one or more hydrogens replaced by an amino group (—$N^+R_8R_9R_{10}$) or by a group —$OR_{11}$, with the proviso that:
      A. if $R_{1-6}$ is a bivalent group then this comprises two groups $R_{1-6}$, which together with at least one of the atoms written in bold letters in formula I form a 5 or 6 membered ring, and
      B. both $R_5$ and $R_6$ can not be selected among methyl and ethyl,
   f. $R_{7-11}$ are selected among the same groups as $R_{1-6}$,
   g. X is —OH or —$NR_{12}R_{13}$, $R_{12-13}$ being selected among the same groups as $R_{1-6}$,
   h. anion exchangers which have been prepared by coupling triethanol amino to cellulose via epoxide are not included.

3. Process according to claim 2, characterized in that B is replacing $R_1$ or $R_2$.

4. Process according claim 2, characterized in that B is a linear, branched or cyclic saturated hydrocarbon chain optionally disrupted by ether oxygen atoms and which optionally has one or more hydrogens replaced by hydroxyl.

5. Process according to claim 2, characterized in that B is —$CH_2CHOHCH_2$—O—$CH_2$—, —$CH_2CHOHCH_2$—O—($CH_2$)$_4$—O—$CH_2$—, —$CH_2$—.

6. Process according to claim 2, characterized in that n is 1 and $R_{1-4}$ are hydrogen.

7. Process according to claim 2, characterized in that $R_5$ and/or $R_6$ is hydrogen.

8. Process according to claim 2, characterized in that X is a hydroxyl group.

9. Process according to claim 2, characterized in that at least one of $R_{5-6}$ contains a group —$N^+R_8R_9R_{10}$) or —$OR_{11}$ at a distance of two carbon atoms away from the nitrogen atom to which $R_{5-6}$ bind, wherein $R_{8-11}$ are selected among the same groups as $R_1$, $R_2$, $R_5$ and $R_6$.

10. The process according to claim 9, wherein $R_{8-11}$ are selected from the group consisting of $C_{1-6}$ alkyl and hydrogen.

11. Process according to claim 2, characterized in that the ligand is selected among:
—$CHOHCH_2NH_2$; —$CHOHCH_2NH(CH_2)_3NH(CH_2)_3NH_2$; —$CHOHCH_2N[(CH_2)_3NH_2]_2$;

—CHOHCH$_2$NH[C(CH$_3$)$_3$];
—CHOHCH$_2$NHCH$_2$CH$_2$OH; —CHOHCH$_2$N(CH$_2$CH$_2$OH)$_2$;
—CHOHCH$_2$NHC(CH$_2$OH)$_3$; —CHOHCH$_2$NHCH(CH$_2$OH)$_2$; —CHOHCH$_2$NHCH$_2$CH$_2$CH$_3$;
—CHOHCH$_2$NHCH$_2$CHOHCH$_2$OH; —CHOHCH$_2$NHC(CH$_3$)(CH$_2$OH)$_2$;
—CHOHCH$_2$NHCH$_2$(CHOH)$_4$CH$_2$OH;
—CHOHCH$_2$N[C(CH$_2$OH)$_3$](CH$_2$)$_3$NHC(CH$_2$OH)$_3$.

12. Process according to claim 2, characterized in that a peptide is separated off and that the anion exchanger exhibits ligands selected among:
—CHOHCH$_2$NH$_2$; —CHOHCH$_2$NH(CH$_2$)$_3$NH(CH$_2$)$_3$H$_2$; —CHOHCH$_2$NHCH$_2$CH$_2$OH;
—CHOHCH$_2$NHCH(CH$_2$OH)$_2$;
—CHOHCH$_2$NHCH$_2$CHOHCH$_2$OH;
—CHOHCH$_2$NHC(CH$_3$)(CH$_2$OH)$_2$; —CHOHCH$_2$NHC(CH$_2$OH)$_3$;
—CHOHCH$_2$N[(CH$_2$OH)$_3$](CH$_2$)$_3$NHC(CH$_2$OH)$_3$.

13. Process according to claim 2, characterized in that nucleic acid is separated off and that the anion exchanger exhibits ligands selected among:
—CHOHCH$_2$NH[C(CH$_3$)$_3$]; —CHOHCH$_2$NHCH(CH$_2$OH)$_2$;
—CHOHCH$_2$NHC(CH$_2$OH)$_3$;
—CHOHCH$_2$NHCH$_2$CH$_2$OH;
—CH$_2$CHOHCH$_2$NHCH$_2$CH$_2$CH$_3$.

14. Process according to claim 2, characterized in that nucleic acid is separated off by adsorption to the ion exchanger and that adsorbed nucleic acid subsequently is eluted by
a. an agent which breaks hydrogen bonds, and/or,
b. salt and/or
c. increasing of pH so that the ligands are completely or partially unloaded.

15. The process according to claim 14, wherein the agent which breaks hydrogen bonds is urea, guanidine or a mixture thereof.

16. Process according to claim 2, characterized in that the nucleic acid is a synthetic oligonucleotide.

17. The process according to claim 2, wherein B is silane, carboxylic acid ester (—COO—), or carboxylic acid amide (—CONH—).

18. The process according to claim 2, wherein R$_{7-11}$ are selected from the group consisting of unsubstituted C$_{1-6}$ alkyl and hydrogen.

19. Process according to claim 1, characterized in that a peptide is separated off by adsorption to the anion exchanger and that adsorbed peptide is eluted by
a. an agent which breaks hydrogen bonds, and/or
b. salt, and/or
c. change of pH.

20. The process according to claim 19, wherein the agent which breaks hydrogen bonds is urea, guanidine or a mixture thereof.

21. Process according to claim 1, characterized in that a peptide is separated off and that the peeptide is applied to the anion exchanger in a solution having an ionic strength of ≧15 mS/cm.

22. Anion exchanger characterized in that it has the structure

FORMULA I ligand        ligand arm (B)
              plus matrix (M)

where
a. — means that the ligand arm B is replacing a group R$_{1-6}$ or a hydrogen in any of the groups R$_{1-6}$ in the ligand,
b. M is a polymer matrix containing further anion exchanging ligands,
c. B is an organic structure which lacks hydrolytically unstable structures, and which contains hydrocarbon chains selected among the same carbon chains as R$_{1-4}$,
d. n is an integer of 1 or 2, typically 1,
e. i. R$_1$, R$_2$, R$_3$ and R$_4$ are selected among hydrogen and linear, branched or cyclic saturated or unsaturated hydrocarbon group, which can be monovalent or bivalent, with a carbon chain which optionally is disrupted by one or more amino nitrogen- or ether oxygen atoms (—NR$_7$— and —O— respectively) and/or has one or more hydrogens replaced by an amino group (—N$^+$R$_8$R$_9$R$_{10}$) or by a group —OR$_{11}$, with the proviso that
   A. if any of the groups is bivalent then this comprises two groups R$_{1-6}$, which together with at least one of the atoms written in bold letters in formula I form a 5 or 6 membered ring,
   ii. R$_5$ and R$_6$ are selected among the same groups as R$_{1-4}$ with the provisos that
   B. if one or two of the groups R$_5$ and R$_6$ contain one or more nitrogen atoms then at least one of the groups also contains one or more oxygen atoms (—OR$_{11}$, where R$_{11}$ is according to paragraph f below),
   C. both R$_5$ and R$_6$ cannot at the same time be selected among methyl and ethyl,
f. R$_{7-11}$ are selected among the same groups as R$_{1-4}$,
g. X is —OH or —NR$_{12}$R$_{13}$, wherein R$_{12}$ and R$_{13}$ are selected among the same groups as R$_{1-6}$,
h. anion exchangers prepared by coupling of triethanol amine to cellulose via a reaction with epoxide are not included.

23. Anion exchanger according to claim 22, characterized in that B replaces R$_1$ or R$_2$.

24. Anion exchanger according to claim 22, characterized in that B is a linear, branched or cyclic saturated hydrocarbon chain which optionally is disrupted by ether oxygen atoms and which optionally has one or more hydrogens replaced by hydroxyl.

25. Anion exchanger according to claim 22, characterized in that B is —CH$_2$CHOHCH$_2$—O—CH$_2$—; —CH$_2$CHOHCH$_2$—O—(CH$_2$)$_4$—O—CH$_2$—; or —CH$_2$—.

26. Anion exchanger according to claim 22, characterized in that n is 1 and that R$_{1-4}$ are hydrogen.

27. Anion exchanger according to claim 22, characterized in that R$_5$ and/or R$_6$ is hydrogen.

28. Anion exchanger according to claim 22, characterized in that the ligand is selected among:
—CHOHCH$_2$NH$_2$; —CHOHCH$_2$N[CH$_2$)$_3$NH$_2$]$_2$; —CHOHCH$_2$NH[C(CH$_3$)$_3$];

—CHOHCH$_2$NHCH$_2$CH$_2$OH; —CHOHCH$_2$N(CH$_2$CH$_2$OH)$_2$; —CHOHCH$_2$NHC(CH$_2$OH)$_3$; —CHOHCH$_2$NHCH(CH$_2$OH)$_2$; —CHOHCH$_2$NHCH$_2$CHOHCH$_2$OH; —CHOHCH$_2$NHC(CH$_3$)(CH$_2$OH)$_2$; —CHOHCH$_2$NHCH$_2$(CHOH)$_4$CH$_2$OH; —CHOHCH$_2$N[C(CH$_2$OH)$_3$](CH$_2$)$_3$NHC (CH$_2$OH)$_3$; —CHOHCH$_2$NHCH$_2$CH$_2$CH$_3$.

29. The anion exchanger according to claim 22, wherein B is silane, carboxylic acid ester (—COO—), or carboxylic acid amide (—CONH—).

30. The anion exchanger according to claim 22, wherein R$_{7-11}$ are selected from the group consisting of unsubstituted C$_{1-6}$ alkyl and hydrogen.

* * * * *